(12) United States Patent
Jacquet-Lagreze

(10) Patent No.: US 10,932,693 B2
(45) Date of Patent: Mar. 2, 2021

(54) DEVICE, SYSTEM AND METHOD FOR EVALUATING THE MICROCIRCULATION OF BLOOD IN A TISSUE

(71) Applicant: Matthias Jacquet-Lagreze, Lyons (FR)

(72) Inventor: Matthias Jacquet-Lagreze, Lyons (FR)

(\*) Notice: Subject to any disclaimer, the term of this patent is extended or adjusted under 35 U.S.C. 154(b) by 636 days.

(21) Appl. No.: 15/532,283

(22) PCT Filed: Dec. 2, 2015

(86) PCT No.: PCT/EP2015/078433
§ 371 (c)(1),
(2) Date: Aug. 15, 2017

(87) PCT Pub. No.: WO2016/087556
PCT Pub. Date: Jun. 9, 2016

(65) Prior Publication Data
US 2018/0103873 A1    Apr. 19, 2018

(30) Foreign Application Priority Data

Dec. 2, 2014 (FR) ...................................... 1461821

(51) Int. Cl.
*A61B 5/021* (2006.01)
*A61B 5/103* (2006.01)
(Continued)

(52) U.S. Cl.
CPC .......... *A61B 5/1032* (2013.01); *A61B 5/0053* (2013.01); *A61B 5/0077* (2013.01); *A61B 5/0082* (2013.01); *A61B 5/02007* (2013.01); *A61B 5/0261* (2013.01); *A61B 5/441* (2013.01); *A61B 5/0088* (2013.01)

(58) Field of Classification Search
None
See application file for complete search history.

(56) References Cited

U.S. PATENT DOCUMENTS 6,631,288 B1    10/2003    Bain
2004/0249290 A1    12/2004    Shani
(Continued)

FOREIGN PATENT DOCUMENTS

WO    00/60349    10/2000

OTHER PUBLICATIONS

International Search Report for corresponding International PCT Application No. PCT/EP2015/078433, pp. 1-3.

*Primary Examiner* — Marjan Fardanesh
(74) *Attorney, Agent, or Firm* — Hauptman Ham, LLP

(57) ABSTRACT

A device for evaluating the microcirculation of blood in human or animal tissue. The device having a housing with an open end for contact with said tissue and thus delimit a study area of said tissue. The device including a light-emission means toward the study area, image-acquisition means of the study area, compression means of at least one determined zone inside the study area, control means controlling the application of said controlled pressure to said zone, then removal of said controlled pressure and image acquisition on said study area exposed to said light, data-processing means using the images acquired to calculate at least one parameter relative to the discoloration and/or the recoloration of said tissue. The compression means calibrated to apply controlled pressure to said zone and retractable to leave said compression zone and/or said study area accessible to said light and/or to the image-acquisition means.

27 Claims, 4 Drawing Sheets

Figure 1A:
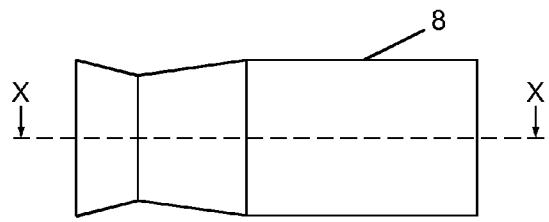

(51) Int. Cl.
*A61B 5/00* (2006.01)
*A61B 5/02* (2006.01)
*A61B 5/026* (2006.01)

(56) References Cited

U.S. PATENT DOCUMENTS

2006/0234383 A1 10/2006 Gough
2009/0143655 A1 6/2009 Shani
2012/0220878 A1 8/2012 Sullivan
2014/0081161 A1 3/2014 Kuno

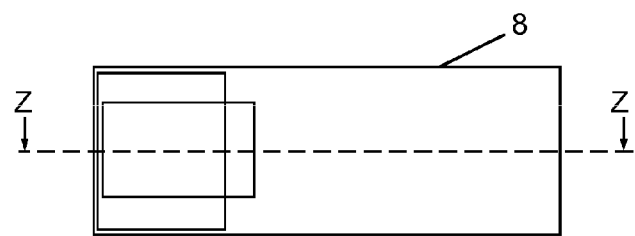
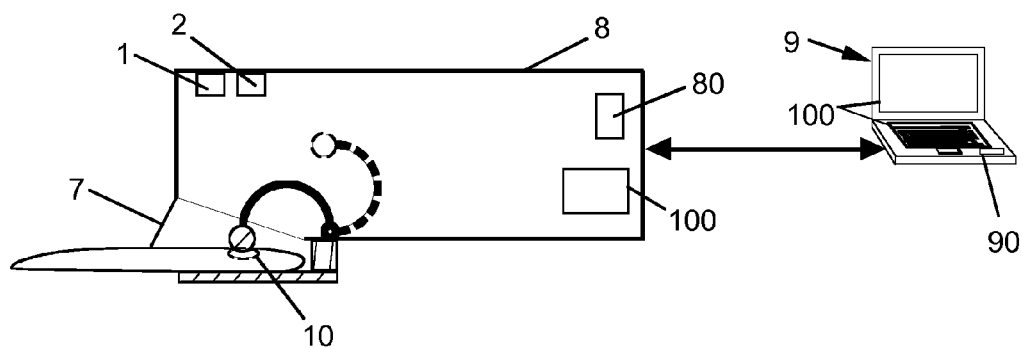
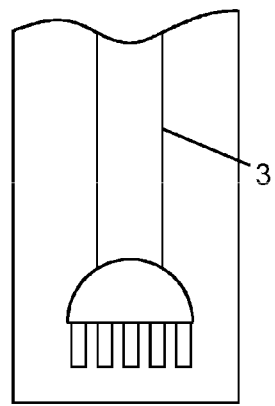
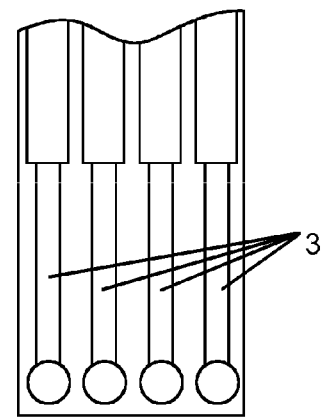

DEVICE, SYSTEM AND METHOD FOR EVALUATING THE MICROCIRCULATION OF BLOOD IN A TISSUE

TECHNICAL FIELD OF THE INVENTION

The present invention relates to the field of evaluating the microcirculation of blood in tissues, in particular for mucosas, preferably intra-buccal, such as for example the cheek mucosa (from the cheek) or gingival (from the gum) but also other mucosas such as the conjunctival (from the eyelid), or for the skin. The studied tissue is preferably a tissue easily accessible on the patient, even when he is unconscious. The invention is particularly adapted to evaluate microcirculation in patients on life support, for example those suffering acute circulatory failure, especially during septic shock. In fact, septic shock is an acute circulatory failure, causing haemodynamic, metabolic and visceral disorders, generally in a context of sepsis (general and serious infection syndrome of the organism by infectious germs). The present invention also applies to haemodynamic and theracanic monitoring of circulatory failures (septic, cardiogenic, hypovolemic or obstructive shock) or in at-risk situations for haemodynamic monitoring, such as for example during anaesthesia for high-risk surgery. Also, the present invention applies to all clinical situations where microcirculatory alteration is considerable, such as for example in metabolic disorders (diabetes, HTA, hypercholesterolemia) or vasculitides. The invention could play a role in theracanic monitoring or prognostic evaluation of these diseases. It also enables evaluating of the state of hydration (especially in paediatrics). In surgery, it could evaluate the viability of grafts and the efficacy of anastomoses (flap surgery, skin grafts, organ graft). The invention can also serve to evaluate ischemic problems, especially mesenteric (to evaluate the viability of the digestive serous membrane and aid the theracanic care) or in the ischaemia of members or advanced arterial diseases.

TECHNOLOGICAL BACKGROUND OF THE INVENTION

A problem in the field of monitoring patients, especially on life support, relates to circulatory failures which can be defined as an acute tissular deficiency in oxygen. All mechanisms of shock (hypovolemic, obstructive or distributive) are accompanied by tissular hypoperfusion (insufficient perfusion) which results from a drop in cardiac output by dysfunction of the cardiac pump or is linked to hypovolemia, arterio-venous vasodilation or the association of these three mechanisms. The persistence of tissular ischaemia leads to the appearance of hypoxic cellular lesions and is accompanied frequently by an inflammatory systemic reaction likely to cause or aggravate visceral lesions. This blood hypoperfusion can cause mottling which are traces on the skin, comparable to marbled veins. Observation of such a symptom therefore provides an indication of circulatory failure.

In general, this problem of circulatory failure can be evaluated according to a macrocirculatory approach or a microcirculatory approach. The macrocirculatory approach is based on measuring parameters such as arterial pressure, cardiac output, heart rate. Indeed, the macrocirculation relates to the macroscopic parameters of circulation, that is, arterial pressure, cardiac output, central venous pressure, heart rate, etc. Measurements are generally taken on the heart or the large vessels. The microcirculatory approach relates to microcirculation starting at the level of the arterioles (generally having a diameter less than 100 micrometers) and continues with the capillaries (between 7 and 20 micrometers for the smallest) where exchanges are made with the cells. Its evaluation is made on the organs, the mucosas or the skin. The microcirculatory approach is therefore based on physical examination of the patient, especially for evaluating the extension of mottling or evaluating the TRC: cutaneous (or capillary) recoloration time. This term of TRC was defined for the first time in 1947 as being the time taken by the capillary bed to resume its colour after being whitened by pressure. The TRC is evaluated in general by the clinician who applies strong pressure with the index finger or thumb to the skin of the patient (conventionally on the finger or on the thorax), then quickly removes the pressure and measures the time the skin takes to regain its initial colour, either by counting or with a chronometer. This technique can also be used on the mucosas but its execution is more complex. It is a fact that the longer the TRC the greater the microcirculatory alteration.

The dissociation between macrocirculation and microcirculation is explained by the microcirculatory shunt large capillaries will be the seat of a rise in rate to the detriment of a whole network of other capillaries, which ends in a drop in perfusion of tissues without variation in cardiac output. In acute circulatory failures, such as for example sepsis, it is a fact that microcirculation and macrocirculation are dissociated and monitoring of patients therefore cannot be based on macrocirculatory evaluation only.

This general problem is accompanied by the problem of difficulty in evaluating microcirculation. In particular, clinical evaluation of the TRC is subject to considerable imprecision, especially by the fact that pressure, cutaneous compression time, ambient light, or even skin temperature are some parameters which can vary and influence the TRC. Thus, methods aiming to evaluate microcirculation more reliably have been developed in the prior art. For example, the prior art discloses, especially in application WO2009/053920A1, a measuring apparatus for cutaneous recoloration time (TRC) in a digital manner for evaluating the state of hydration. This apparatus functions typically by applying controlled pressure to a member (the foot) and by using polarised light illuminating the skin and a sensor which transforms the signal reflected in the form of an image. This type of solution also has the drawback of being costly, especially due to the use of polarised light and corresponding sensors, but also due to necessary data processing. Also, this solution has the drawbacks of being too bulky and consequently does not allow evaluation of microcirculation on various cutaneous surfaces inaccessible to such apparatus. Similarly, this apparatus does not take measurements over the entire cutaneous surface of the body, due to the necessity of counterpressure (the segment of member with the skin surface to be analysed is wedged between the 2 parts of the apparatus to maintain controlled pressure). Finally, this apparatus is made to evaluate hydration and allows cutaneous measurements only without taking into account variations of the TRC linked to temperature (in particular because it is designed to evaluate hydration in children suffering from diarrhoea and exhibiting little or no fever contrary to sepsis).

On the other hand, methods aiming to eliminate problems of measuring techniques of the TRC have been developed in the prior art. For example, videomicroscopy techniques for evaluating microcirculation by an imaging of microvessels of the order of 20 micrometers are known. However, these techniques have the drawbacks of being costly and need interpretation by an expert, with long analysis times, risks of compression artefact and absence of the possibility of continuous measuring. Many probes of Doppler laser type are also known for evaluating microcirculation from a pulsatile signal, in different places (such as for example the digestive tract, the mouth, the genital organs, the cutaneous surface, a wound, etc.) These probes are generally based on the principle of photoplethysmography (PPG) or the Laser Doppler Flowmetry (LDF). The principle of PPG uses cutaneous reflexion of infrared light at the level of the intradermal venous plexus. Laser Doppler Flowmetry (LDF) (or velocimetry) is used in haemodynamic research as a technique for partially quantifying blood flow in human tissues such as the skin. The beam emitted by a low-strength laser (in general a laser diode) penetrates the skin to be sufficiently dispersed with a Doppler frequency shift by the red blood cells. These techniques also have the drawback of being costly. Also, these techniques use measuring from a pulsatile signal while microcirculation is not this, which likens these techniques to evaluating perfusion closely upstream of the microcirculation. On the other hand, these techniques have risks of compression artefact in keeping contact with the probe with the measured zone.

In this context, it is significant to provide a low-cost and reliable solution for evaluating microcirculation.

GENERAL DESCRIPTION OF THE INVENTION

A first aim of the present invention is to obviate at least one of the drawbacks of the prior art by proposing an evaluation device of microcirculation, in particular low-cost and/or reliable and/or utilisable on various portions of the body, even those difficult to access.

This aim is achieved by an evaluation device of microcirculation of blood of human or animal tissue, in particular a mucosa or the skin, characterised in that it comprises a housing comprising an open end, intended to be placed in contact with said tissue and thus delimit a study area of said tissue, the device comprising:
   light-emission means towards the study area,
   image-acquisition means of the study area,
   compression means of at least one determined zone inside the study area, said compression means being calibrated to apply controlled pressure to said zone and retractable to leave said compression zone and/or said study area, accessible, preferably fully accessible, to said light and/or the image-acquisition means,
   control means controlling application of said controlled pressure to said zone during a first determined time, then removal of said controlled pressure and the image acquisition on said study area exposed to said light during a second determined time, data-processing means using the images acquired to calculate at least one parameter relative to the discoloration and/or the recoloration of said tissue.

According to another feature, at least one human-machine interface provides a user of the device with said parameter relative to the discoloration and/or the recoloration of said tissue.

According to another feature, said parameter is a recoloration time of said tissue.

According to another feature, the housing is fitted at its open end with a skirt delimiting said study area and flexible for limiting variations in pressure due to application of the device against said tissue by a user.

According to another feature, said skirt is interchangeable, of material type, disposable and disinfected or sterile.

According to another feature, the compression means comprise at least one piston whereof the end intended to be in contact with the tissue is interchangeable, of material type, disposable and disinfected or sterile.

According to another feature, said compression means are calibrated by the fact that they comprise at least one piston mounted on a calibrated compression spring.

According to another feature, said compression means are mounted on a return spring activated on completion of said first determined time to return said piston and cancel said controlled pressure to said zone.

According to another feature, said compression means comprise at least one piston activated by thrust means calibrated by a manometer or a pressure sensor, for example piezoelectric.

According to another feature, said compression means comprise counterpressure means for limiting variations in pressure due to application of the device against said tissue by a user.

According to another feature, said compression means comprise several pistons applying the same controlled pressure to several zones in said study area.

According to another feature, said compression means comprise a single piston fitted with several projections applying the same controlled pressure to several zones in said study area.

According to another feature, said compression means comprise several pistons applying different controlled pressures to several zones in said study area.

According to another feature, the data-processing means calculate at least one parameter relative to the discoloration and/or the recoloration of said tissue on each of said zones and compare this calculated parameter between said zones (10) to calculate at least one parameter relative to the homogeneity between the calculated parameters on the different zones.

According to another feature, the device comprises, at the open end, at least one contact sensor with said tissue to trigger the measuring of the first and second determined times.

According to another feature, the device is dimensioned, at least at the level of the open end, for application of calibrated pressure to an intra-buccal, gingival or conjunctival mucosa.

According to another feature, the device comprises heating means of said study area.

According to another feature, said control means are integrated into said housing.

According to another feature, said data-processing means are integrated into said housing.

Another aim of the present invention is to obviate at least one of the drawbacks of the prior art by proposing a system for evaluating microcirculation, in particular low-cost and/or reliable and/or utilisable on various portions of the body, even those difficult to access.

This aim is achieved by a system for evaluating microcirculation of blood in human or animal tissue, in particular a mucosa or the skin, characterised in that it comprises at least one device according to some embodiments of the invention, cooperating with at least one computer device comprising data-processing means calculating said parameter relative to the discoloration and/or the recoloration of said tissue.

According to another feature, said computer device comprises a human-machine interface providing a user of the device with said parameter relative to the discoloration and/or the recoloration of said tissue.

According to another feature, said computer device manages control means of the device and uses a first determined time and a second determined time for controlling application of said controlled pressure to said zone during a first determined time, then removal of said controlled pressure and the image acquisition on said study area exposed to said light during a second determined time.

Another aim of the present invention is to obviate at least one of the drawbacks of the prior art in proposing a method for evaluating microcirculation, in particular low-cost and/or reliable and/or utilisable on various portions of the body, even those difficult to access.

This aim is achieved by a method for use of a device or a system for evaluating microcirculation of blood in human or animal tissue, in particular a mucosa or the skin, characterised in that it comprises the following steps:

Application of said device to said tissue;
Application of calibrated pressure to said tissue during a first determined time by the compression means located at the open end of said device;
Illumination of said tissue by a light at the open end of said device and acquisition of images of said tissue by said device, during a second determined time;
Removal of the compression means outside the field of acquisition of images;
Calculation of at least one parameter relative to the discoloration and/or the recoloration of said tissue following removal of said calibrated pressure.

According to another feature, the method comprises an analysis of the images acquired by the device, this analysis comprising the following steps:

measuring reference coloration of the tissue prior to application of said calibrated pressure;
calculation of the difference in coloration of the tissue after application of said calibrated pressure relative to the reference coloration, several successive times after the removal of said calibrated pressure;
determination of a recoloration time, by measuring the time when said coloration difference falls again below a determined threshold.

According to another feature, the method comprises a display of information relative to the recoloration time.

According to another feature, the method comprises a comparison of the coloration of the tissue at at least one determined time close to the recoloration time relative to the reference coloration, to determine hypercoloration if the coloration at this determined time is intenser than the reference coloration.

According to another feature, the method comprises a display of information relative to the hypercoloration.

According to another feature, the method comprises calculation of at least one parameter relative to the discoloration and/or the recoloration of said tissue on a plurality of zones of said study area and calculation of at least one parameter relative to the homogeneity between the calculated parameters on the different zones.

According to another feature, the method is executed by at least one device according to some embodiments of the invention or at least one system according to some embodiments of the invention.

DESCRIPTION OF THE ILLUSTRATIVE FIGURES

Figures 1B, 1C:
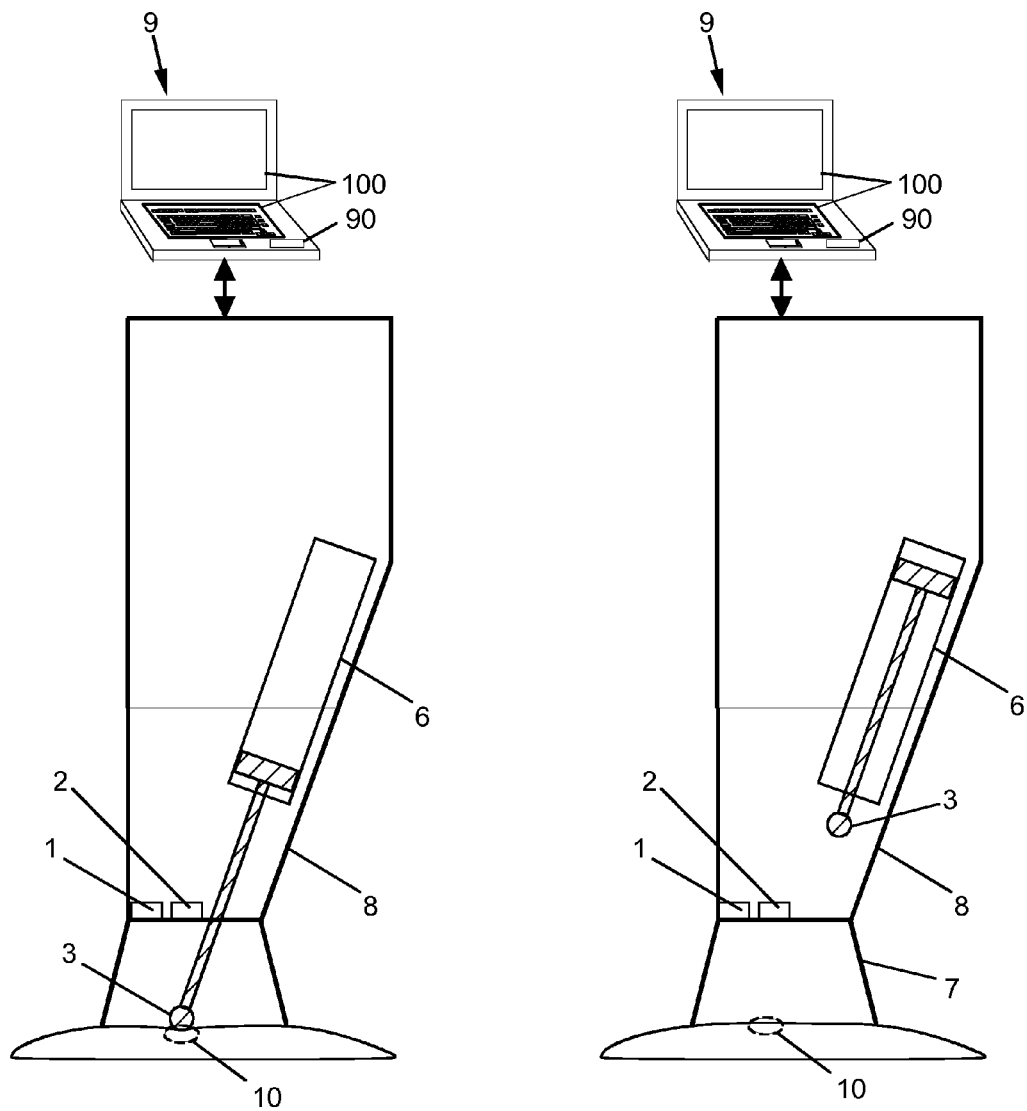
Figure 2A:
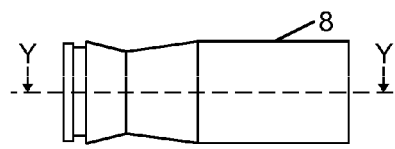
Figure 2B:
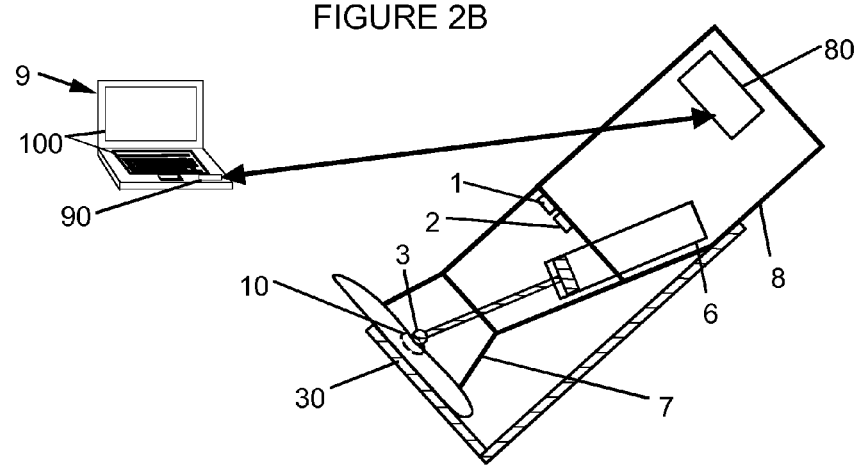
Figure 2C:
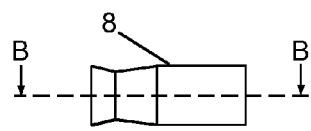
Figure 2D:
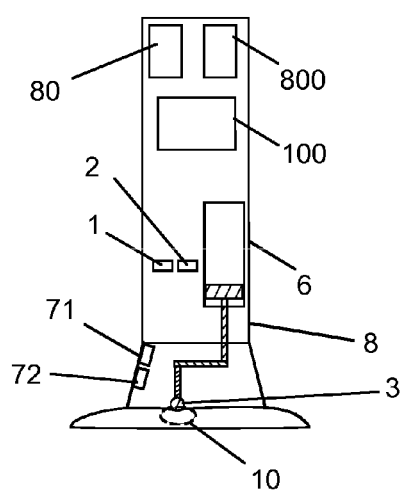
Figure 2E:
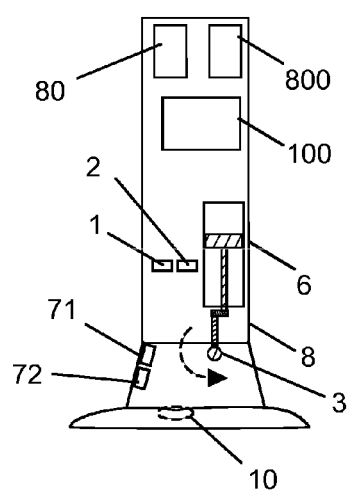
Figure 4A:
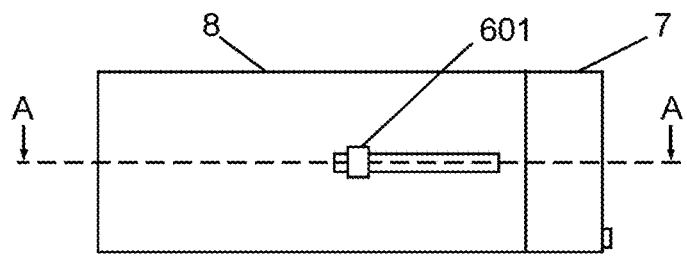
Figure 4B:
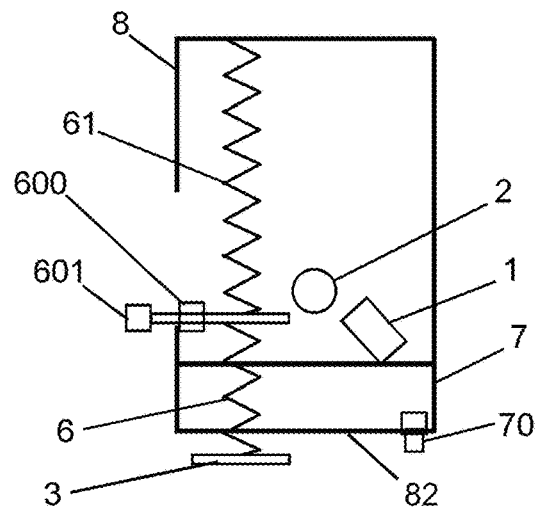
Figure 4C:
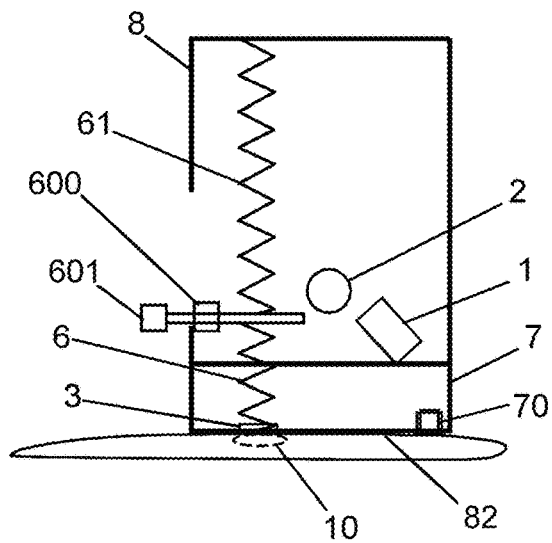
Figure 4D:
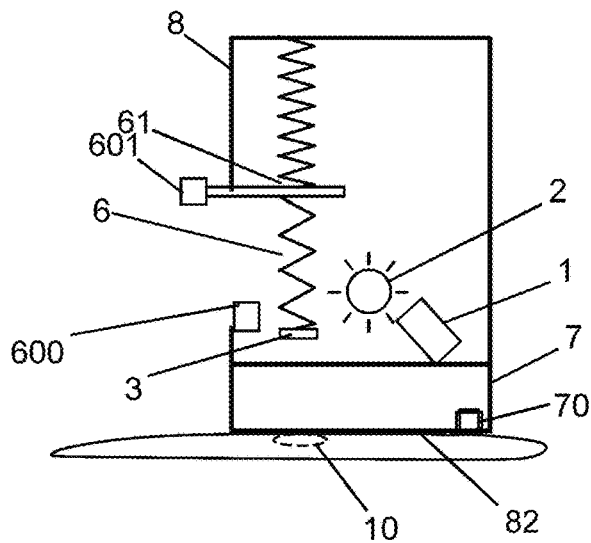

Other features and advantages of the present invention will appear more clearly upon reading the following description, given with reference to the appended drawings, in which:

FIG. 1A represents a profile view of an evaluation device of microcirculation according to various embodiments, FIGS. 1B and 1C represent sectional views, according to the cutting plane X-X of FIG. 1A, of an evaluation device of the microcirculation according to various embodiments, respectively during and after application of calibrated pressure to a tissue;

FIGS. 2A and 2C represent a profile view of devices for evaluating microcirculation according to various embodiments, FIG. 2B represents a sectional view according to the cutting plane Y-Y of FIG. 2A, FIGS. 2D and 2E represent sectional views according to the cutting plane B-B of FIG. 1A, of an evaluation device of the microcirculation according to different embodiments and according to the cutting plane X-X of FIG. 1A, of an evaluation device of microcirculation according to different embodiments;

FIG. 3A represents a profile view of an evaluation device of microcirculation according to various embodiments, and FIG. 3B represents a sectional view of this device according to the cutting plane Z-Z of FIG. 3A, FIGS. 3C and 3D show perspective views of the end of compression means according to different embodiments;

FIG. 4A represents a profile view of an evaluation device of the microcirculation according to various embodiments, FIGS. 4B, 4C and 4D represent sectional views, according to the cutting plane A-A of FIG. 4A, of an evaluation device of the microcirculation according to various embodiments, respectively after arming of the device, during application of calibrated pressure to a tissue and after disarming of the device.

DESCRIPTION OF PREFERRED EMBODIMENTS OF THE INVENTION

In general, the present invention relates to a device, a system and a method for evaluating microcirculation of blood in human or animal tissue, in particular a mucosa or the skin. In general, the relevant mucosas will be buccal mucosas, such as gingival or cheek mucosas, especially because they are easy to access even in an unconscious patient (for example under sedative) and/or enable precise estimation of microcirculation, but the invention can of course be used on other mucosas, for example selected for their easy access or their relevance to the prognosis of patients and/or their treatments.

In some embodiments, an illustrative and non-limiting example of which is shown in the figure, the invention relates to an evaluation device for microcirculation of blood in human or animal tissue, in particular a mucosa or the skin. Such a device is characterised in that it comprises a housing (8) comprising an open end (82), intended to be placed in contact with said tissue and thus delimit a study area of said tissue, the device comprising:

light-emission means (2) towards the study area,
image-acquisition means (1) of the study area,
compression means (3, 6) of at least one determined zone (10) inside the study area, said compression means (3, 6) being calibrated to apply controlled pressure to said zone (10) and retractable to leave said compression zone, or even said study area as a whole, accessible to said light and/or to the image-acquisition means (1), and preferably fully accessible (without disruption to acquisition and/or illumination),
control means (80, 9) controlling application of said controlled pressure to said zone (10) during a first determined time, then removal of said controlled pressure and image acquisition on said study area exposed to said light during a second determined time, data-processing means (800, 90) using the acquired images to calculate at least one parameter relative to the discoloration and/or the recoloration of said tissue.

The housing is preferably grippable by hand. For example, an ergonomic handle can be provided on the housing which in turn can also have an ergonomic form such as for example a cylindrical form or at least a longitudinally elongated form, for example grippable in a single hand. A form for example of a pen or felt pen thicker than a pen and holding in the hand can be particularly practical. However, various forms of housing are possible and some embodiments allow the housing to be applied to the tissue without being held by a user, especially (though not exclusively) when counterpressure means (30) are provided on the device (such as for example detailed later in the present application). In this way, the device can be kept in contact with the tissue by holding means (of various shapes, such as for example a bandage or an adhesive strip, an adhesive plaster, etc.), or by the fact that it comprises counterpressure means such that the tissue is sandwiched in the device.

In some embodiments, an illustrative and non-limiting example of which is shown in FIG. 2B, said control means (80) are integrated into said housing (8). Such control means (80) preferably comprise controllers for managing the various means present in the device, via adapted connectors. Such control means (80) can comprise data storage and processing means for defining and storing parameters such as the length of application of pressure, illumination of the tissue and image acquisition and thus manage the various means of the device to control its operation. According to preferred cost and complexity, it is possible to limit these control means to the function of regulating the various means of the evaluation device and using the latter under the supervision of a computer device (9), that is, a control device (9) comprising computer means, such as a computer for example, as shown in the illustrative and non-limiting example of FIG. 2B. In this way, in some embodiments, an illustrative and non-limiting example of which is shown in FIG. 2B, said computer device (9) manages control means (80) of the device to control application of said controlled pressure to said zone (10) during a first determined time, then removal of said controlled pressure and the image acquisition on said study area exposed to said light during a second determined time.

In some embodiments, an illustrative and non-limiting example of which is shown in FIGS. 2C and 2D, said data-processing means (800) are integrated into said housing (8). In these embodiments, these data-processing means regulate the control means (80) which manage the other means of the device, which can be substantially autonomous and does not need an additional computer device (9). In some of these embodiments, an illustrative and non-limiting example of which is shown in FIGS. 2C and 2D, the device fitted with such data-processing means (800) comprises a human-machine interface (100) providing a user of the device with said parameter relative to the discoloration and/or the recoloration of said tissue. Such an interface can of course serve to adjust the device and/or the display of other parameters and/or the selection of various measuring protocols, for example stored in a memory of the device.

As an alternative, less costly for the device itself, but needing an additional computer device (9), some embodiments of the invention relate to a system for evaluating microcirculation of blood in human or animal tissue, in particular a mucosa or the skin, characterised in that it comprises at least one device according to some embodiments cooperating with at least one computer device (9) comprising data-processing means (90). These data-processing means (90) calculate said parameter relative to the discoloration and/or the recoloration of said tissue. In some of these embodiments, an illustrative and non-limiting example of which is shown in FIGS. 1B and 10, said computer device (9) comprises a human-machine interface (100) providing a user of the device with said parameter relative to the discoloration and/or the recoloration of said tissue. As mentioned earlier, such an interface can of course serve various functions of regulating, calibration, controlling, selection of measuring sequences, etc. In general, such an interface is known to the expert and the resulting uses do not need to be detailed. Also, figures illustrate a computer display and a keyboard, but it is evident that a touch display is equivalent and as a function of the selected embodiments various functions at this interface and various interface means could be selected (visual, tactile, sound, etc.) In fact, it is possible to simply fit the evaluation device providing sounds (or sound sequences) to indicate to the user which action to perform (apply the device, press more or less, remove the device, etc.) and/or the result of evaluation (for example a short bip for good microcirculation and a long bip for poor microcirculation, if such a vague indication is satisfactory).

In some embodiments, the light-emission means comprise at least one light source. Light emission in the visible or infrared (or near infrared) spectrum is preferably selected. It is possible to provide a polychromatic spectrum or not, such as for example white or monochromatic light. Advantageously, such emission means therefore comprise (or even are formed by) a simple and low-cost light source.

On the other hand, in some embodiments, the image-acquisition means comprise (or even are formed by) at least one video or photo device. In fact, in such embodiments, especially when a simple and low-cost light source is used, the invention takes advantage of simple images acquired a low cost, such as for example by means of a camera or optoelectronic sensor, such as a cMOS sensor (Complementary Metal Oxide Semiconductor) for example, enabling acquisition of video sequences or images in burst mode. Various embodiments therefore take advantage of a simple and low-cost light source which is sufficient for a light sensor for simply measuring the coloration of the tissue before and after application of calibrated pressure. This measuring of coloration can simply relate to an estimation, from the images acquired, of the colour saturation, especially saturation of the magenta tint, but can of course relate to saturation of various tints. On the other hand, it is also understood that the invention takes advantage of these light emission and image acquisition means which can both be very reduced in size. In fact, such a light source can take the form of a lightbulb of small size (of the order of the size of the end of a ballpoint pen) or even of an LED (or DEL in French for <<diode électroluminescente>>) and can therefore not exceed 5 millimetres in diameter. Similarly, the image acquisition means can comprise a sensor, for example of cMOS type as detailed earlier, the size of which can be highly restricted, for example of the order of 5 millimetres in diameter also. On the other hand, although designated as performing an image acquisition, the acquisition means can in fact be sensors of simple lights not necessarily capturing all wavelengths. Finally, calibrated pressure can be applied to the tissue by means of a rod or piston of restricted dimensions, such as for example the end of a 1 ml syringe piston. In general, the choice will be to apply calibrated pressure to a surface between 25 mm$^2$ and 100 mm$^2$, preferably 50 mm² (i.e. on a surface of around 5 millimetres in diameter, or 1 centimetre in diameter), but it is possible to utilise pressure to a more extended surface, especially (but not only) in various embodiments detailed later where the heterogeneity is also studied on several zones within the study area. Advantageously, the combination of such simple means and reduced size produces a low-cost device of reduced dimensions (at least at the level of the open end where measuring is done) making it easy to use, but above all usable over a wide range of tissues, even those difficult to access. In fact, with such dimensions of the light source, the sensor and the rod, the resulting device can advantageously have an open end whereof the diameter does not exceed a centimetre or a few centimetres only (for example a total size of the order of that of a thumb). In this way, the device can easily be used on buccal mucosas (cheek or gingival especially) or conjunctival mucosas (by lifting the eyelid for example, especially if the patient is intubated and fitted with apparatus making access to his mouth difficult), in addition to any other tissue such as the skin, for instance. Thus, in some embodiments, illustrative and non-limiting examples of which are shown in the figures attached to the present application, the device is dimensioned, at least at the level of the open end, for application of calibrated pressure to an intra-buccal, gingival or conjunctival mucosa.

Advantageously, the device utilises compression means which applies calibrated pressure to a determined zone of the tissue and which retract outside the field monitored by the acquisition means. This removal precisely studies the compressed zone and optionally the zone which encloses it, in a given study area. Indeed, the majority of clinical data indicates that it is recoloration of the compressed zone which is a determining factor, as it reveals critical parameters such as mortality, gravity of the shock (septic, hemorrhagic, etc.). It is therefore useful to have access directly to the zone which has been compressed (and optionally the one adjacent), without disturbance of the illumination by an object and without perturbation of image acquisition by material interposed in between the acquisition means and the tissue. Indeed, devices are known in which transparent material is interposed in between the acquisition means for pressing on the tissue by means of the latter, but this solution disrupts measuring by this material which needs to adapt the acquisition means and above all, of which transparency and sterility are unstable since it becomes contaminated on contact with the tissue studied. Also, since hypercoloration occurs sometimes during compression of tissues which is too high for the physiological state of these tissues, it can be useful to compare the coloration differences between the zone which has been compressed to the one on the side. Finally, by use of retractable compression means, the present invention allows to make an evaluation of the recoloration according to various techniques. A first technique consists of making the acquisition of the coloration control value (or "coloration reference") prior to application of pressure in the zone which will be compressed, which is advantageous for example if the light is not fully uniform in the field of acquisition over the entire possible study surface. A second technique consists of making the acquisition of the coloration control value around the compressed zone, which can be advantageous in case of hypercoloration or instability of the user prior to application of pressure. A third technique consists of not really making acquisition of a control value prior to or around, but sticking to the compressed zone by taking only the coloration measurement once the zone is recoloured, by taking the coloration value at the plateau, for example by calculating the derivative of the coloration signal and detecting its return to zero. These techniques are cited here by way of illustration to show the advantages of the use of retractable compression means but they are not exhaustive or limiting. On the other hand, the use of these retractable compression means outside the field of acquisition, while precisely studying the compressed zone in addition to adjacent zones in the study area, has the advantage of the use of several compression zones and to refine the analysis, such as for example in some embodiments described in the present application.

Preferably, as the device is intended to be placed in contact with the patient (and often in contact with mucosas) the choice is (and at a minimum, in general) to use means classified as "semi-critical" and/or "median infectious risk" and/or "sole usage with intermediate disinfection". The outright choice can be to use sterile means, but it seems generally sufficient to use equipment known for being defined as of "material type, disposable and disinfected or sterile". Thus, the end of the rod or piston used for applying the calibrated pressure will preferably be interchangeable, of material type, disposable and disinfected or sterile. Here the term "of type" is used to indicate that the exact denomination is of minor importance and that this is above all about creating a protection function against germs. In some embodiments, an illustrative and non-limiting example of which is shown in FIGS. 1A and 1B for example, the compression means (3, 6) comprise at least one piston (3) the end of which intended to be in contact with the tissue is interchangeable, of material type, disposable and disinfected or sterile.

In some embodiments, an illustrative and non-limiting example of which is shown in FIGS. 1A, 1B, 2A and 2B, the housing (8) is fitted at its open end with a skirt (7) delimiting said study area. This skirt keeps the study area perfectly dark and subjects it only to the light of the device (without external parasite light) for optimising the evaluation of microcirculation. Also, such a skirt is preferably selected flexible to limit variations in pressure due to application of the device against said tissue by a user. Preferably, in these embodiments, said skirt (7) is also interchangeable, of "material type, disposable and disinfected or sterile".

With respect to the compression means themselves, the expert will understand that various structures are possible for applying calibrated pressure and the present application details various advantageous embodiments which must not be interpreted limitingly. In some embodiments, said compression means (3, 6) are calibrated by the fact that they comprise at least one piston (3) mounted on a calibrated compression spring (6). It will also be evident that the terms piston or rod or others used in the present application must not be considered limitingly and that they optionally designate any structure, of any shape, capable of applying pressure, such as for example a rod end or stick or any structure such as for example a simple plate. In fact, in the examples in FIGS. 4B, 4C and 4D pressure is applied by a plate mounted on elastic means (6, 61), designated hereinbelow "springs" even though it should in fact be interpreted in a non-limiting manner.

In some embodiments, an illustrative and non-limiting example of which is shown in FIGS. 1B and 1C, said compression means (3, 6) comprise at least one piston (3) activated by thrust means (6) calibrated by a manometer or a pressure sensor, for example piezoelectric. Various motor means are possible for the thrust means and means using translation of a piston or rod can be used, but it is possible to use rotation, such as for example shown in FIG. 3B or a combination of translation and rotation such as for example shown in FIGS. 2C and 2D. In this example of FIGS. 2C and 2D the piston comprises a right-angled end for applying pressure opposite the field of the light source and the image-acquisition means. This arrangement provides an alternative to the embodiments where the piston is not right-angled and must therefore be installed in bias relative to the rest of the device to leave the field free after application of pressure, such as for example shown in FIGS. 1B and 1C. This alternative, more complex due to the two types of movement needed, can remain advantageous to limit the dimensions of the device as it is unnecessary to place the piston obliquely. In this example of a combination of movements, the translation serves to exert thrust to apply the calibrated pressure, and the rotation serves to thrust the end of the piston outside of the field of illumination and/or of the field of image acquisition. It will also be noted that it is possible to advantageously limit the size of the device, not putting the piston obliquely but putting the light and acquisition means placed obliquely, as shown in FIGS. 4B, 4C and 4D for measuring the zone. Finally, in some embodiments, an illustrative and non-limiting example of which is shown in FIG. 3B, the compression means are activated in rotation, for example by a curved rod which retracts into the width of the housing and deploys as far as the study area by rotation around an axis near the open end. Such an arrangement also lets the rod leave the field free to light and image acquisition.

In some embodiments, the housing (8) comprises an open end (82) in the extension of the device (i.e. a distal open end, for example in the longitudinal axis), as shown in the majority of the figures. However, to be able to study surfaces to which access could be made more easily according to an axis non-perpendicular to the study area, or even parallel to the surface, some embodiments provide an open end (82) at the level of the lateral wall of the housing (and not the distal wall). An illustrative and non-limiting example of such embodiments is shown in FIG. 3B showing that the light means (2) and image acquisition means (1) are placed opposite the lateral opening (82), perpendicularly to the longitudinal axis of the device. In this example of FIG. 3B, the compression means are activated in rotation, but it is possible to use means activated in translation, especially obliquely, as in other embodiments illustrated in the present application. Similarly, this example illustrates a device fitted with counterpressure means (30) the utility of which is detailed later on, but this example is not limiting. In particular, these counterpressure means (30) are oriented towards the distal end (fixed before of the opening and extending right in front of the opening) but it is possible to orient them in the other direction, that is, towards the proximal end instead of the distal end or according to various orientations, such that their fastening to the housing is provided for appropriate use (as a function of the tissue to be studied). Also, of course such counterpressure means (30) in these embodiments having lateral opening can be omitted.

In some embodiments, especially among embodiments where said compression means (3, 6) comprise at least one piston (3) mounted on a calibrated compression spring (6), said compression means (3, 6) are mounted on a return spring (61) activated on completion of said first determined time to return said piston (3) and cancel said controlled pressure to said zone (10). An illustrative and non-limiting example of these embodiments is shown in FIGS. 4B, 4C and 4D. In these examples, said compression means (3, 6), mounted on a return spring (61), must be armed by the user by arming means (600, 601), for example such as a cursor (601) accessible on the wall of the housing (8) and driven by sliding to elongate the return spring (61). The cursor (601) is then kept in an armed position by a latch (600). Such a latch (600) allows relaxing the cursor (601), preferably automatically under the control of control means (9, 80) when the application time of the pressure has elapsed. This relaxing with such a latch allows rapid actuation on completion of said first determined time to return said piston (3) and cancel said controlled pressure to said zone (10). In some of these embodiments it is possible to provide pressure control means, for example using several latches (600) or a controllable position latch. In fact, if the complete course of the cursor (601) bearing the compression spring (6) is defined for the spring to be able to apply a determined (maximal) pressure when the open end of the device is applied to the tissue, it is possible to adjust the position at which the cursor is to be stopped such that the pressure applied is less (than the maximal pressure). Graduations, for example with pressure values, could also be placed on the housing to guide the user. Even in these latter adjustable variants, it will be noted that these embodiments have the advantage of being simple and low-cost to make and use, and provide a reliable evaluation of the recoloration. In most embodiments, the present invention also allows execution of a method very easy for the user who has only to apply the device to the tissue and let it then supply result.

In some embodiments, an illustrative and non-limiting example of which is shown in FIGS. 4B, 4C and 4D, at the open end the device comprises at least one contact sensor (70) with said tissue to trigger measurement of the first and second determined times. Such a contact sensor can also be or comprise a pressure sensor for verifying that the user himself is not applying excessive pressure which risks influencing the pressure, preferably calibrated, applied by the device. Such a sensor is of course particularly advantageous in the case of use of a return spring, to trigger counting of the application time and automatic stopping of compression. It will also be noted that in those embodiments comprising such a return spring, a calibrated compression spring is preferably used, but it is possible to replace these springs by any elastic means, preferably having calibrated elasticity, and that the choice can even be made to replace the compression spring (6) by other means, for example the contact sensor (70), preferably when the latter measures the pressure of the contact to apply a correct pressure without overly depending on the skill of the user.

In some embodiments, an illustrative and non-limiting example of which is shown in FIG. 2A, said compression means (3, 6) comprise counterpressure means (30) for limiting the variations in pressure due to application of the device against said tissue by a user. Such counterpressure means (30) can comprise a plate in a stable position relative to the compression means and intended to be placed opposite the compression means to wedge the tissue to be studied in between the compression means and the counterpressure means. The stable position of the counterpressure means lets the calibrated pressure be applied reliably, since it is due only to the compression means pressing the tissue against the counterpressure means. In this way, the pressure exerted by the device is totally independent of the pressure which the user might clumsily exert. It will be noted that the stable position of the counterpressure means relative to the compression means can be adjustable in order to adapt the device to the thickness of the tissues to be wedged between the compression means and the counterpressure means. In such embodiments, the presence of the skirt is not completely necessary, but it can all the same be kept to isolate the study area from the rest of the tissues and above all keep the study area subject to the light source of the device only (no ambient light).

In some embodiments, an illustrative and non-limiting example of which is shown in FIG. 3C, said compression means (3, 6) comprise a single piston (3) fitted with several projections applying the same controlled pressure to several zones (10) in said study area. In such embodiments, it is possible to verify the homogeneity of the reaction of the tissue to pressure, as detailed hereinbelow. In some embodiments, an illustrative and non-limiting example of which is shown in FIG. 3D, said compression means (3, 6) comprise several pistons (3) applying either the same controlled pressure to several zones (10) in said study area, or different controlled pressures to several zones (10) in said study area. The application of different pressures optionally verifies the pertinence of the test for each of the pressures applied. In some of these embodiments, an illustrative and non-limiting example of which is shown in the figure, the data-processing means (800, 90) calculate at least one parameter relative to the discoloration and/or the recoloration of said tissue on each of said zones (10) and calculate at least one parameter relative to the homogeneity between the calculated parameters on the different zones (10). It will be noted that in some embodiments it is possible to also calculate homogeneity on different zones, even if a pressure has been applied to a single given zone. In fact, it is possible to subdivide said zone into several sub-zones and calculate the preferred parameters for each of these sub-zones resulting in comparison of the sub-zones. Preferably, the subdivision between the sub-zones provides a space between each sub-zone so as to avoid coverage between the sub-zones and avoid calculations on sub-zones whereof a portion can have the same properties as the adjacent sub-zone (especially due to blood vessels which can extend over a region common to two sub-zones).

In some embodiments, an illustrative and non-limiting example of which is shown in FIGS. 2C and 2D, the device comprises heating means (71) of said study area. In some embodiments, the device comprises means for measuring temperature (72) of the study area or near the latter such that a corrective factor can be applied to evaluating microcirculation as a function of the temperature measured. Preferably, such a measurement of the temperature is also provided in the embodiments where the device comprises heating means, for example for controlling the need to resort to the latter, deciding on the temperature to apply and controlling the temperature during heating. It will be noted that this is about heating, but that in fact delicate reheating to avoid harming the tissues is meant here. Such heating or reheating means are therefore preferably fitted with progressive diffusion means of heat towards the tissue, or at a minimum fitted with means for protection of the tissue against burns. Such embodiments are particularly advantageous (but not only) in the case of use on a tissue such as skin which is subjected to thermoregulation phenomena, that is, mechanisms which keep the organism at a constant temperature (constriction of cutaneous capillaries during cold and dilation to heat). In this way, controlling the temperature can take this into account in the evaluation and adjusting the temperature ideally prevents these phenomena from disrupting measuring by the device.

In some embodiments, as already mentioned, at least one human-machine interface (100) provides a user of the device with said parameter relative to the discoloration and/or the recoloration of said tissue. In some embodiments, said parameter is at least one recoloration time of said tissue or an index of recoloration or microcirculation determined on the basis of time calculated and knowledge of circulatory phenomena. In fact, the device according to various embodiments allows easy use on patients and lets various embodiments of a method be executed for evaluating microcirculation, as a function of measurements taken. In this way, in some embodiments, the invention relates to a method for evaluating microcirculation of blood in human or animal tissue, in particular a mucosa or the skin, characterised in that it comprises the following steps:

Application of the device to the tissue;

Application of calibrated pressure to said tissue during a first determined time by compression means (3, 6) located at the open end of an evaluation device of the microcirculation of blood, applied to said tissue;

Illumination of said tissue by a light at the open end of said device and acquisition of images of said tissue by said device, during a second determined time;

Calculation of at least one parameter relative to the discoloration and/or the recoloration of said tissue following removal of said calibrated pressure.

Advantageously, the method conducts a step in the device for removal of the compression means (3, 6) outside the field of acquisition of images. The advantages of this step are detailed earlier in reference to the device and have no need of being repeated.

In some embodiments, the method comprises an analysis of the images acquired by the device, this analysis comprising the following steps:

measuring reference coloration of the tissue prior to application of said calibrated pressure;

calculation of the difference in coloration of the tissue after application of said calibrated pressure relative to the reference coloration, several successive times after the removal of said calibrated pressure;

determination of a recoloration time, by measuring the time when said coloration difference falls again below a determined threshold.

As detailed in reference to the device, various techniques are possible and the measuring step of the reference coloration is not necessarily carried out on the compression zone, or even may not be necessary if the recoloration criterion is simply used by the derivative of the measured signal. In general, the recoloration of the tissues follows a fairly linear and rapid evolution, such that if suffices to measure the recoloration time. The fact of determining when coloration has returned to normal (or near normal, with a determined tolerance threshold) is therefore sufficient. But, it is of course possible to measure several different times, especially times determined by reference to a logarithmic curve if this proves necessary. In some embodiments, the method comprises a display of information relative to the recoloration time, that is, either the time itself or a determined index such as for example an index for evaluating the microcirculation. In fact, the device itself or the computer control device (9) can store a correspondence table between the data relative to time and to microcirculation, but the user generally knowledgeable often has no need for an index and knows how to base his conclusions on the value of recoloration time.

In those embodiments where microcirculation is evaluated over several zones (10) or several sub-zones within the studied zone (10), it is understood that the method is applied in the same way, but analysis will be reiterated for each sub-zone or zone. Also, analysis allows comparison of zones or sub-zones to each other and calculation of a homogeneity factor, for example such as the difference between the longest time and the shortest time between two zones/sub-zones, preferably divided by the average of times of the zones/sub-zones.

In some embodiments, the method comprises a comparison of the coloration of the tissue at at least one determined time close to the recoloration time (for example the time at which the coloration difference has become lower than the threshold, as explained above) relative to the reference coloration, to determine hypercoloration if the coloration at this determined time is intenser than the reference coloration. In fact, it is often observed that the tissues in patients of some conditions can exhibit hyperaemia, that is, a rise in coloration relative to the base state, generally witnessing an endothelial alteration (of the wall of the vessels). In this way, in some embodiments the method comprises a display of information relative to hypercoloration (or hyperaemia) via the human-machine interface.

It is evident from the above description for the device and the system that according to various embodiments the method is executed by at least one device according to some embodiments of the invention or at least one system according to some embodiments of the invention. The expert will therefore understand all the implications of the various embodiments of device and system in terms of method.

The present application describes various technical features and advantages with reference to the figures and/or various embodiments. Those skilled in the art will understand that the technical features of a given embodiment can in fact be combined with features of another embodiment unless explicitly stated otherwise or unless it is evident that these features are incompatible or that the combination does not provide a solution to at least one of the technical problems mentioned in the present application. In addition, the technical features described in a given embodiment can be isolated from the other technicalfeatures of this embodiment unless explicitly stated otherwise.

It must be obvious to those skilled in the art that the present invention allows embodiments in many specific forms without departing from the field of application of the invention as claimed. Consequently, the present embodiments must be considered as illustrations, but can be modified in the area defined by the scope of the appended claims, and the invention must not be limited to the details given above.

The invention claimed is:

1. A device for evaluating the microcirculation of blood in human or animal tissue, the device comprises a housing comprising an open end, configured to be placed in contact with said tissue and thus delimit a study area of said tissue, the device comprising:
    a light-emitter configured to emit light towards the study area,
    an image sensor configured to capture an image of the study area,
    a piston,
    a manometer or a pressure sensor configured to control a pressure applied by the piston through an actuator, wherein actuation of the actuator is configured to control the piston calibrated to exert a calibrated pressure to at least one determined zone inside said study area, the piston being configured to remove away from said at least one determined zone and/or said study area and to be not in contact with said at least one determined zone and/or said study area, the removing of the piston causing said at least one determined zone and/or said study area to be fully accessible to said light-emitter and/or to the image sensor,
    a controller configured to control the application of said calibrated pressure to said at least one determined zone during a first determined time, then removal of said calibrated pressure and image acquisition on said study area exposed to said light during a second determined time, and
    a data processor configured to use the images acquired to calculate at least one parameter relative to the discoloration and/or the recoloration of said tissue.

2. The device according to claim 1, wherein at least one human-machine interface provides a user of the device with said parameter relative to the discoloration and/or the recoloration of said tissue.

3. The device according to claim 1, wherein said parameter is a recoloration time of said tissue.

4. The device according to claim 1, wherein the housing is fitted at its open end with a skirt delimiting said study area and flexible to limit variations in pressure due to application of the device against said tissue by a user.

5. The device according to claim 4, wherein said skirt is interchangeable, of material type, disposable and disinfected or sterile.

6. The device according to claim 1, wherein the piston is at least one piston whereof an end configured to be in contact with the tissue is interchangeable, of material type, disposable and disinfected or sterile.

7. The device according to claim 1, wherein the piston is calibrated by the fact that it is at least one piston mounted on a calibrated compression spring.

8. The device according to claim 7, wherein the piston is mounted on a return spring activated on completion of said first determined time to return said piston and cancel said calibrated pressure to said at least one determined zone.

9. The device according to claim 1, wherein the piston comprises counterpressure means for limiting variations in pressure due to application of the device against said tissue by a user.

10. The device according to claim 1, wherein the piston is several pistons applying the same calibrated pressure to several zones in said study area.

11. The device according to claim 1, wherein the piston is a single piston fitted with several projections applying the same calibrated pressure to several zones in said study area.

12. The device according to claim 1, wherein the piston is several pistons applying different calibrated pressures to several zones in said study area.

13. The device according to claim 1, wherein
    the at least one determined zone includes a plurality of determined zones, and
    the data processor is configured to
        calculate at least one parameter relative to the discoloration and/or the recoloration of said tissue on each of said plurality of determined zones and
        compare this calculated parameter between said plurality of determined zones to calculate at least one parameter relative to homogeneity between the calculated parameters on different zones among the plurality of determined zones.

14. The device according to claim 1, wherein the device comprises, at the open end, at least one contact sensor with said tissue to trigger the measuring of the first and second determined times.

15. The device according to claim 1, wherein the device is dimensioned, at least at a level of the open end, for application of the calibrated pressure to an intrabuccal, gingival or conjunctival mucosa.

16. The device according to claim 1, wherein the device comprises a heater configured to heat said study area.

17. The device according to claim 1, wherein the controller is integrated into said housing.

18. The device according to claim 1, wherein the data processor is integrated into said housing.

19. A system for evaluating the microcirculation of blood of human or animal tissue wherein the system comprises at least one device according to claim 1 cooperating with at least one computer device comprising a data processor configured to calculate said parameter relative to the discoloration and/or the recoloration of said tissue.

20. The system according to claim 19, wherein said computer device comprises a human-machine interface providing a user of the device with said parameter relative to the discoloration and/or the recoloration of said tissue.

21. The system according to claim 19, wherein said computer device is configured to manage the controller of the device and use a first determined time and a second determined time to control application of said calibrated pressure to said zone during a first determined time, then removal of said calibrated pressure and the image acquisition on said study area exposed to said light during a second determined time.

22. A method for use of a device according to claim 1, for evaluating the microcirculation of blood of human or animal tissue, in particular a mucosa or the skin, wherein the method comprises:

application of said device to said tissue;

application of the calibrated pressure to said tissue during a first determined time, by the piston located at the open end of said device;

illumination of said tissue by a light at the open end of said device and acquisition of images of said tissue by said device, during a second determined time;

removal of the piston outside the field of acquisition of images; and calculation of at least one parameter relative to the discoloration and/or the recoloration of said tissue following removal of said calibrated pressure.

23. The method according to claim 22, wherein the method comprises an analysis of the images acquired by the device, this analysis comprising:

measuring reference coloration of the tissue prior to application of said calibrated pressure;

calculation of the difference in coloration of the tissue after application of said calibrated pressure relative to the reference coloration, several successive times after the removal of said calibrated pressure;

determination of a recoloration time, by measuring the time when said coloration difference falls again below a determined threshold.

24. The method according to claim 23, wherein the method comprises a display of information relative to the recoloration time.

25. The method according to claim 23 wherein the method comprises a comparison of the coloration of the tissue at at least one determined time close to the recoloration time relative to the reference coloration, to determine hypercoloration if the coloration at this determined time is more intense than the reference coloration.

26. The method according to claim 25, wherein the method comprises a display of information relative to the hypercoloration.

27. The method according to claim 22, wherein the method comprises calculation of at least one parameter relative to the discoloration and/or the recoloration of said tissue on a plurality of zones in said study area and calculation of at least one parameter relative to the homogeneity between the calculated parameters on the different zones.

* * * * *